United States Patent
Gross

(10) Patent No.: US 7,262,178 B2
(45) Date of Patent: Aug. 28, 2007

(54) TREATMENT OF SEPSIS AND SEPTIC SHOCK

(75) Inventor: Richard A. Gross, Plainview, NY (US)

(73) Assignee: Polytechnic University, Brooklyn, NY (US)

( * ) Notice: Subject to any disclaimer, the term of this patent is extended or adjusted under 35 U.S.C. 154(b) by 433 days.

(21) Appl. No.: 10/807,961

(22) Filed: Mar. 24, 2004

(65) Prior Publication Data

US 2004/0214795 A1    Oct. 28, 2004

Related U.S. Application Data

(60) Provisional application No. 60/457,070, filed on Mar. 24, 2003.

(51) Int. Cl.
*A61K 31/7024*    (2006.01)
*A61K 31/7028*    (2006.01)

(52) U.S. Cl. .......................... 514/53; 536/4.1

(58) Field of Classification Search ............ 514/53
See application file for complete search history.

(56) References Cited

U.S. PATENT DOCUMENTS

| | | |
|---|---|---|
| 5,514,661 A | 5/1996 | Piljac |
| 5,597,573 A | 1/1997 | Kamireddy et al. |
| 5,648,343 A | 7/1997 | Carlson |
| 6,057,302 A * | 5/2000 | Borzeix ............. 514/54 |

OTHER PUBLICATIONS

Kandil et al., "Sophorolipids block lethal effects of septic shock" Journal of the American College of Surgeons (Sep. 2003) vol. 197, No. 3S, pp. S40-S41.*
Gorin, P.A. et al., Can. J. Chem., vol. 39, p. 846 (1961).
Davila, A.M. et al., J. Chromatogr., vol. 648, p. 139 (1993).
Tulloch, A.P. et al., Can. J. Chem., vol. 40, p. 1326 (1962).
Tulloch, A.P. et al., Can J. Chem., vol. 46, p. 3337 (1968).
Zhou, Q.-H., et al., J. Am. Oil Chem. Soc., vol. 72, p. 67 (1995).
Rau, U. et al., Biotechnol. Lett., vol. 18, p. 149 (1996).
Bisht, K.S. et al., J. Org. Chem, vol. 64, pp. 780-789 (1999).

* cited by examiner

*Primary Examiner*—Shaojia Anna Jiang
*Assistant Examiner*—Eric S. Olson
(74) *Attorney, Agent, or Firm*—Laurence P. Colton; Smith, Gambrell & Russell LLP

(57) ABSTRACT

A method and composition for the treatment of humans or animals for septic shock and sepsis using a mixture of sophorolipids.

6 Claims, 2 Drawing Sheets

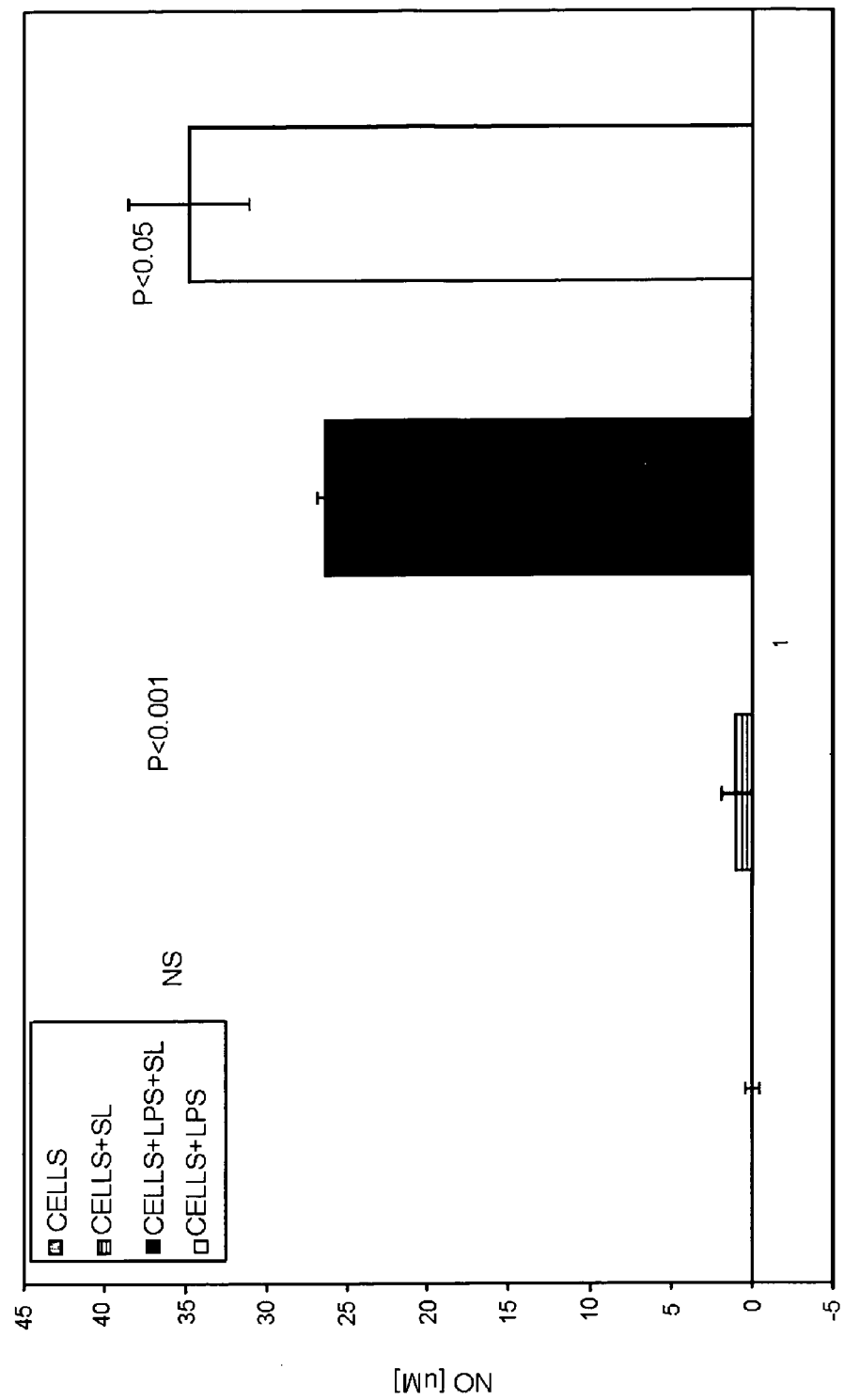

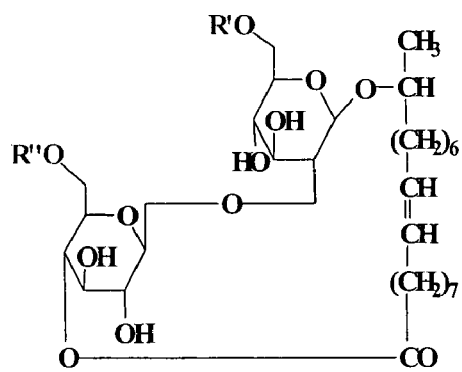
1. R' = R" = Ac or H
2. R' = Ac; R" = H
3. R' = H; R" = Ac
4. R' = R" = H
FIG. 2A
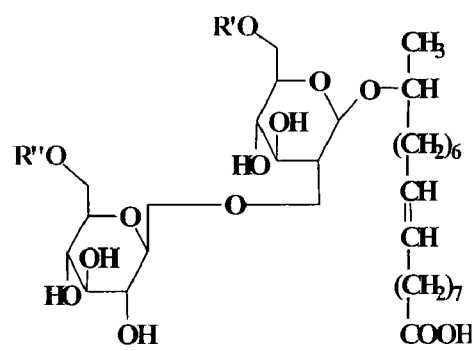
5. R' = R" = Ac or H
6. R' = Ac; R" = H
7. R' = H; R" = Ac
8. R' = R" = H
FIG. 2B
FIG. 2

TREATMENT OF SEPSIS AND SEPTIC SHOCK

STATEMENT OF RELATED APPLICATIONS

This application is a nonprovisional patent application based on and claiming priority on U.S. Provisional Patent Application No. 60/457,070 having a filing date of 24 Mar. 2003.

BACKGROUND OF THE INVENTION

1. Technical Field

The present invention generally relates to the technical field of compounds and methods for the treatment or prophylaxis of sepsis and toxic shock. The present invention more specifically relates to the technical field of using a sophorolipids mixture and the administration of such a mixture for the treatment or prophylaxis of animals and humans for sepsis and septic shock.

2. Prior Art.

Septic shock and sepsis can be a life threatening systemic bacterial intoxication. Septic shock and sepsis can be associated with organ dysfunction, hypoperfusion, or hypotension. With early and intensive treatment including the use of antibiotics and intensive life support, the serious consequences of septic shock and sepsis can sometimes be avoided. However, despite the use of such treatments, the mortality rate remains high and in some cases can range from 25% to 75%.

Chills, fever, nausea, vomiting, diarrhea, and prostration characterize clinical symptoms of septic shock and sepsis. The subsequent development of septic shock is characterized by tachycardia, tachypnea, hypotension, peripheral cyanosis, mental obtundation, and oliguria. As septic shock and sepsis progresses, the clinical symptoms can include heart failure, respiratory insufficiency, and coma. Mortality often results from pulmonary edema, cardiac arrhythmia and failure, disseminated intravascular coagulation with bleeding, or cerebral anoxia.

The pathogenesis of septic shock and sepsis usually results from the systemic and unregulated host response to the bacterial antigens, which results in an elaborate and extensive array of chemical mediators. Specifically, the host's immune system is triggered by the lipopolysacchraride (LPS) from the outer membrane of gram-negative bacteria. The LPS over-stimulates the hosts' immune response by activating monocytes/macrophages, neutrophils, and endothelial cells. The activation of these cells results in an elaborate and extensive array of proinflammatory mediators, which can include cytokines, lipids, oxygen and nitrogen radical intermediates, complement, catecholamines, histamines, and others. The chemical mediators can cause local damage to cells and systemic toxic effects.

First described in 1961, sophorolipids occur as a mixture of macrolactone and free acid structures that are acetylated to various extents at the primary hydroxyl position of the sophorose ring. Gorin, P. A. et al., Can. J. Chem., vol. 39, p. 846 (1961). Careful examinations have revealed that at least eight structurally different sophorolipids are produced. Davila, A. M. et al., J. Chromatogr., vol. 648, p. 139 (1993). The main component of sophorolipids is 17-hydroxyoctadecanoic acid and its corresponding lactone. Tulloch, A. P. et al., Can. J. Chem., vol. 40, p. 1326 (1962) and Tulloch, A. P. et al., Can J. Chem., vol. 46, p. 3337 (1968).

Work has been carried out to tailor sophorolipid structure during in vivo formation, mainly by the selective feeding of different lipophilic substrates. Zhou, Q.-H., et al., J. Am. Oil Chem. Soc., vol. 72, p. 67 (1995). Also unsaturated C-18 fatty acids of oleic acid may be transferred unchanged into sophorolipids. Rau, U. et al., Biotechnol. Lett., vol. 18, p. 149 (1996). However, while physiological variables during fermentation have provided routes to the variation of sophorolipid composition, this has not led to well-defined pure compounds.

Existing data suggests that glycolipids may be useful in treating very severe immune disorders. For example, glycolipids have been reported to be of interest for in vivo cancer treatment/antitumor cell activity, treatment of autoimmune disorders, in vivo and in vitro antiendotoxic (septic) shock activity, regulation of angiogenesis, and apoptosis induction, all by cytokine activity. See, e.g., U.S. Pat. No. 5,597,573 to Massey, U.S. Pat. No. 5,514,661 to Piljac, U.S. Pat. No. 5,648,343 to Carlson, and the references cited in notes 9-13 of Bisht, K. S. et al., J. Org. Chem, vol. 64, pp. 780-789 (1999). However, it has not been shown that sophorolipids can achieve the same results.

Thus, it can be seen that there is need for improved and new compounds and methods for the prophylaxis and treatment of septic shock and sepsis. It is to this need that the present invention is directed.

BRIEF SUMMARY OF THE INVENTION

The invention is a novel class of sophorolipids compounds and mixtures, and their use as a treatment or prophylaxis for the treatment of humans and animals for sepsis and septic shock. The invention has proven successful for sepsis and septic shock induced by certain cytokines and for microbial toxins such as bacterial endotoxins, and is suitable for sepsis and septic shock induced by is other toxins. The present invention makes use of sophorolipids as anti-septic shock agents. More particularly, 8-10 sophorolipids and additional biosynthetically modified structures are used as anti-septic shock agents. One method of producing sophorolipids suitable with the present invention is through microbial resting cells of *Candida bombicola*. The method involves administering a therapeutically effective dose of a sophorolipids mixture to an animal or human. The sophorolipids mixture can be administered to the patient intraperitoneally, but it is contemplated that the sophorolipids mixture can be administered intraarterially and intravenously.

BRIEF SUMMARY OF THE FIGURE

FIG. 1 is a graph of the NO production of cells and cells exposed to SL and/or LPS.

FIG. 2 are representative structures of sophorolipids produced by *Candida bombicola*, with FIG. 2A showing a lactonic sophorolipid and FIG. 2B showing an open-ring sophorolipid.

DETAILED DESCRIPTION OF THE PREFERRED EMBODIMENTS

1. Introduction.

Embodiments of the present invention are sophorolipids mixture and methods of using such mixtures for the prophylaxis or treatment of animals and human for sepsis and septic shock induced by a host's immune response.

The invention comprises the treatment or prophylaxis of sepsis by administering a sophorolipid mixture in an effective therapeutic amount to humans or animals. Those of ordinary skill in the art know techniques and general formulations suitable for administering the sophorolipid compositions. For example, in certain embodiments, the sophorolipid composition can be administered intraperitoneally, intraarterially, or intravenously. The amount of amount of the sophorolipid composition administered, namely the therapeutically effective amount, is an amount sufficient to mediate inflammation of the patient. Preferably, such an effective amount can range from about 2 to 30 mg/kg body weight. It is contemplated that persons of ordinary skill in the art could determine an effective amount greater or less than the preferred range.

2. Illustrative Methods of Sophorolipid Fermentation and Preparation of Sophorolipids.

The present invention makes use of sophorolipids as anti-septic shock agents. More particularly, 8-10 sophorolipids and additional biosynthetically modified structures are used as anti-septic shock agents. One method of producing sophorolipids suitable with the present invention is through microbial resting cells of Candida bombicola. The chemical composition of sophorolipids produced by these cells is constituted by a disaccharide sugar viz. sophorose and a fatty acid or an ester group. For example, lactonic sophorolipid was separated from a crude mixture of sophorolipids synthesized by the fermentation of Candida bombicola. A lactonic fraction was collected separately and all other fractions were mixed to form a non-lactonic sophorolipid mixture. Ethyl 17-L-[(2'-O-β-D-glucopyranosyl-β-D-glucopyranosyl)-oxy]-cis-9-octadecenoate then was synthesized and then further treated to obtain ethyl 17-L-[(2'-O-β-D glucopyranosyl-β-D-glucopyranosyl)-oxy]-cis-9-octadecenoate 6',6"-diacetate. Ethyl 17-L-[(2'-O-β-D-glucopyranosyl-β-D-glucopyranosyl)-oxy]-cis-9-octadecenoate-6"-acetate also was synthesized by adding lipase to a solution of ethyl ester (325.4 mg) and vinyl acetate (230.9 μl) in dry tetrahydrofuran (THF) (5 ml), and further treatment. FIG. 2 shows representative structures of sophorolipids produced by Candida bombicola, with FIG. 1A showing a lactonic sophorolipid and FIG. 1B showing an open-ring sophorolipid.

Sophorolipids useful in this invention can be synthesized by fermentation of Candida bombicola. To synthesize such sophorolipids, a fermentation media composed of glucose 100 g, yeast extract 10 g, urea 1 g and oleic acid 40 g in 1000 ml of water can be made. After 7 days of fermentation, sophorolipid was extracted thrice using ethyl acetate. The extracts were pooled and the solvent then was removed. The obtained product was then washed with hexane to remove the residual fatty acids. This was "natural" sophorolipid. The sophorolipid was dried in a vacuum desiccator.

Column chromatographic separations were performed over silica gel 70 (Aldrich Chemical Co.) to separate lactonic sophorolipid from the crude mixture. 50 g of silica gel was used to pack a glass column (5 cm×50 cm) in the eluent ($CHCl_3$/MeOH mixture). 200 ml of eluent was run through the column before the natural mixture (dissolved in a minimal volume of eluent) was loaded onto the top of the column matrix. Different fractions were subsequently eluted (1 mL/min). A lactonic fraction was collected separately and all other fractions were mixed to form non-lactonic sophorolipid mixture.

Ethyl 17-L-[(2'-O-β-D-glucopyranosyl-β-D-glucopyranosyl)-oxy]-cis-9-octadecenoate can be synthesized by adding 2 g of dry crude sophorolipid and 2.5 mL 0.021 N sodium ethoxide in methanol solution to a 100 mL round-bottomed flask equipped with a reflux condenser. The reaction assembly was protected from atmospheric moisture by a $CaCl_2$ guard tube. The reaction mixture was refluxed for 3 hr, cooled to room temperature (30° C.), and acidified using glacial acetic acid. The reaction mixture was concentrated by rotoevaporation and poured with stirring into 100 mL of ice-cold water that resulted in the precipitation of the sophorolipid ethylester as a white solid. The precipitate was filtered, washed with ice-water, and lyophilized.

The synthesized Ethyl 17-L-[(2'-O-β-D-glucopyranosyl-β-D-glucopyranosyl)-oxy]-cis-9-octadecenoate (500 mg) was dissolved in 20 mL of dry THF. To this solution were added vinyl acetate (2 mL) and Novozym 435 (1 g), and the suspension was stirred magnetically at 35° C. for 96 hr. The enzyme was filtered off, the solvent was evaporated, and the product was purified by column chromatography (eluent $CHCl_3$/MeOH, 9:1) to give 490 mg of Ethyl 17-L[(2'-O-β-D glucopyranosyl-β-D-glucopyranosyl)-oxy]-cis-9-octadecenoate 6',6"-diacetate.

The synthesis of other related compounds, such as methyl- and butyl-based compounds, can be accomplished by substituting sodium methoxide or sodium butoxide respectively for the sodium ethoxide, resulting in sophorolipid methylester and sophorolipid butylester, respectively. The amount of dry natural sophorolipid and the amount and normality of the sodium $(CH_2)_n$oxide can be varied appropriately by those of ordinary skill in the art without undue experimentation. Other types of suitable sophorolipids also can be synthesized by those of ordinary skill in the art without undue experimentation.

Hexyl 17-L-[(2'-O-β-D-glucopyranosyl-β-D-glucopyranosyl)-oxy]-cis-9-octadecenoate can be synthesized by adding 2 g of dry natural sophorolipid and 2.5 mL 0.021 N sodium hexanoxide in hexanol solution to a 100 mL round-bottomed flask equipped with a reflux condenser. The reaction assembly was protected from atmospheric moisture by a $CaCl_2$ guard tube. The reaction mixture was refluxed for 3 hr, cooled to room temperature (30° C.), and acidified using glacial acetic acid. The reaction mixture was concentrated by rotoevaporation and poured with stirring into 100 mL of ice-cold water that resulted in the precipitation of the sophorolipid ethylester as a white solid. The precipitate was filtered, washed with ice-water, and lyophilized.

3. Experimental.

In experimental systems using mice and rats, the sophorolipids showed a protective effective against endotoxic/septic shock when administered by intraperitoneal injection. In particular, sophorolipids showed protective activity against the products of gram-negative bacteria in experimental systems. The sophorolipids mixtures of the present invention may be active in similar physiological conditions triggered by other microbial agents.

It is contemplated that the sophorolipids mixtures act on the action mechanism that involves the regulation and modulation of cytokines and nitric oxide (NO) production. More particularly, the sophorolipids are likely to act at one or more of the steps in severe immunological and inflammatory signaling cascades, including, but not limited to, the toll-like receptor pathways, the cytokine pathways, and the iNOS (inducible nitric oxide synthase pathway). The sophorolipids mixtures may provide a protective effect against ongoing endotoxic shock by inhibiting bacterial lipopolysaccharide (LPS)-induced nitric oxide generation by activated macrophages. In vivo and in vitro testing indicates that sophorolipids can have anti-inflammatory and immunomodulation affects and can be therapeutic agents in septicemia or septic shock.

Different structural sophorolipid derivatives and mixtures are likely to have different levels of biological activity. In addition to specific amounts of sophorolipids and the type of free structural sophorolipid derivatives, it is also important to consider the potential biological activity (anti-inflammatory and immunomodulation) of conjugates of sophorolipids to other bioactive compounds that are known to be of immunological importance, such as signaling molecules and cytokines. The other molecule can be linked to the carboxyl group or one or more of the hydroxyl groups of the sophorolipid to create, for example, targeting compounds.

As nitric oxide production is a useful marker of macrophage response to bacterial LPS, the in vitro model system is a valuable tool for examining the modulating effects of sophorolipids on LPS-induced macrophage responses under controlled conditions. Mouse macrophages (RAW 264.7, ATCC) were incubated in the presence of LPS (*Salmonella typhimurium*, Sigma #6511) (50 ng/ml, an optimal dose for inducing NO production), and varying concentrations of sophorolipids (SL, natural mixture), sophorolipid diethyl ester (E), and corresponding sophorolipid diacetate (K). Sophorolipids were added 1.5 hours before, 1.5 hours after, or simultaneously with LPS. Aliquots of culture supernatants were collected after 5 days and NO content was determined by measuring nitrite (modified Griess reaction). Briefly, triplicate 50 µl aliquots of the culture supernatant were mixed in wells of a 96-well microtiter plate with 100 µl of Griess reagent containing a 1:1 (vol/vol) mixture of 1% (wt/vol) sulfanilamide in 30% acetic acid and 0.5% (wt/vol) of N-(-1-Naphthyl)ethylenediamine dihydrochloride in 60% acetic acid. Chromophore generated by the reaction with nitrite was detected spectrophotometrically (550 nm) using a microtiterplate reader ($EL_x$ 800, BioTek Instruments, Winooski, Vt.). The concentration of nitrite was calculated by using calibration with known concentrations of $NaNO_2$. The results clearly showed that natural sophorolipid mixture (SL) and modified structures E and K inhibited LPS-induced NO production in a dose- and time-dependent manner.

The three molecular forms of sophorolipids tested could be rated with respect to the potency of their inhibitory activities as follows: E>SL>K. The greatest and most consistent inhibition was observed with E, reaching a plateau of 60-65% inhibition at 25 ng/ml. SL caused a more limited decrease in NO production, reaching a maximum of about 35% inhibition at 25 ng/ml. Finally, E showed the least inhibitory and the most variable effects on LPS induced NO production by RAW 264.7 cells.

This in vitro model system made it possible to examine in detail the effects of sophorolipids on LPS induced NO production as a marker of the acute inflammatory pathway that leads to septic shock in vivo. NO production appeared to depend on the sequence of addition of sophorolipids relative to LPS. The in vitro effects were most pronounced when sophorolipids were introduced either before or simultaneously with LPS.

The sophorolipids mixtures of the present invention can be mixed with a pharmaceutically acceptable carrier such as, for example purposes only, physiologically compatible buffers such as, but not limited to, solution, physiological saline, a mixture consisting of saline and glucose, heparinized sodium-citrate-citric acid-dextrose solution, alcohols, dimethylsulfoxide (DMSO), and other such acceptable carriers.

The active compounds also can be administered intraperitoneally.

Solutions of the active compounds as freebase or pharmacologically acceptable salts can be prepared in water suitably mixed with a surfactant, such as hydroxypropylcellulose. Dispersions also can be prepared in glycerol, liquid polyethylene glycols, and mixtures thereof, and in oils. Under ordinary conditions of storage and use, these preparations can contain a preservative to prevent the growth of microorganisms.

Sterile injectable solutions can be prepared by incorporating the active compounds in the required amount in the appropriate solvent with various other ingredients, as needed, followed by filtered sterilization. Generally, dispersions can be prepared by incorporating the various sterilized active ingredients into a sterile vehicle that contains the basic dispersion medium and any required other ingredients from those enumerated above. In the case of sterile powders for the preparation of sterile injectable solutions, methods of preparation include vacuum drying and freeze-drying techniques that yield a powder of the active ingredient plus any additional desired ingredient from a previously sterile-filtered solution thereof.

EXAMPLE 1

The sophorolipids mixtures of the invention have antiseptic shock properties, which were confirmed by experiment and observations. The in vivo experiments demonstrated that sophorolipids have a protective effect against ongoing endotoxic shock (see Table 2). Intraperitoneal injection of sophorolipids 1.5 hrs after galactosamine-LPS treatment resulted in 53% lower mortality than that observed among positive control mice (receiving only galactosamine-LPS treatment) or mice treated with sophorolipids 1.5 hrs before or simultaneously with galactosamine-LPS treatment.

The application of sophorolipids can provide a prophylaxis or treatment for septic shock and sepsis. As shown in Table 3 and FIG. 1 and as expected, macrophage cells not exposed to LPS and macrophage cells only exposed to SL do not produce an appreciable amounts of NO. To the contrary, macrophage cells exposed to LPS produce NO. Importantly, a comparison of NO production of macrophage cells exposed to LPS and of the NO production of macrophage cells treated with sophorolipids and exposed to LPS suggests that the sophorolipid application significantly reduces NO production caused by LPS. As NO production is a marker for septic shock and sepsis, the data suggests that sophorolipids can provide a prophylaxis or treatment for septic shock and sepsis.

More specifically, the graph of FIG. 1 is based on experiments measuring the effects of sophorolipids on macrophage cells in culture and on the cells' response to bacterial LPS. FIG. 1 shows several things: first, cells alone do not produce nitric oxide (first bar on the left); second, in the presence of sophorolipid, there is very little increase in nitric oxide production (second bar from the left; NS, not significant statistically; third, LPS causes a dramatic increase in nitric oxide production (fourth bar); and fourth, the presence of sophorolipid significantly reduces nitric oxide production caused by LPS (third bar from the left).

The potential of sophorolipids and emulsans as therapeutic agents was tested on animal models. Specifically, to determine if the mixture acts as antagonists that interfere with the effects of endotoxins, female BALB/c mice (8-10 weeks old) were injected intraperitoneally with sophorolipids (natural mixture) and two structural variants of emulsans (one with and one without protein). The compounds were injected intraperitoneally at 1.0, 0.1 and 0.001 mg per mouse (in saline). These injections were preceded by 1.5 hours with LPS challenges (LT2 *Salmonella typhimurium* LPS isolated by phenol-water method, 0.5 mg/mouse) to induce endotoxin response in combination with galactosamine (Sigma, 18 mg/mouse) to sensitize the animals to the lethal effects of endotoxin. The results are summarized in Table 1. The data shows a clear protective effect of the sophorolipids at the 1 mg dose that was not observed with the emulsan samples.

TABLE 1

Effects of sophorolipid exposures on mortality of galactosamine-endotoxin sensitized mice.

| | #Died/#Total Mice Injected (% mortality) | | |
|---|---|---|---|
| Samples | 1.0 mg/mouse | 0.1 mg/mouse | 0.001 mg/mouse |
| sophorolipid mixture | 1/14(7.1%) | 4/7(57.1%) | 4/7(57.1%) |
| emulsan (deproteinated) | 12/14(85.7%) | 6/7(85.7%) | 4/7(57.1%) |
| emulsan (with protein) | 13/14(92.9%) | 6/7(85.7%) | 4/7(57.1%) |

TABLE 2

Sophorolipid-mediated protection of BALB/c mice against galactosamine-LPS induced endotoxic shock

| Time of injection (hours) | | | Mortality (%) | |
|---|---|---|---|---|
| D-Galactosamine | LPS | SL | | |
| 0 | — | — | 0 | (n = 6) |
| 0 | 0 | — | 83 | (n = 6) |
| 0 | 0 | 1.5 | 30 | (n = 10) |
| 0 | 0 | 0 | 89 | (n = 9) |
| 0 | 1.5 | 0 | 80 | (n = 10) |

Endotoxic shock was induced by intraperitoneal (IP) injection of *Salmonella typhimurium* lipopolysaccharide (LPS) (1 mg/mouse) following sensitization by IP injection of D-galactosamine (18 mg/mouse). Sophorolipids (SL) were injected 1.5 hours before LPS, simultaneously, or 1.5 hours after LPS injection. Data shown are for a representative experiment.

TABLE 3

Sophorolipids and NO Production

| D-Galactosamine | Average uM of NO Production | # of Samples |
|---|---|---|
| Cells | −0.0417 | 3 |
| Cells + SL | 0.931 | 3 |
| Cells + LPS + SL | 26.3 | 3 |
| Cells + LPS | 34.8 | 3 |

LPS: lipopolysaccharide (endotoxin);
SL: Sophorolipids

EXAMPLE 2

The sophorolipids mixtures of the invention also were tested on Sprague Dawley rats. Three groups of 25 rats were subjected to cecal ligation and puncture (CLP) and subjected to sepsis. Sepsis was allowed to run its course in the first group of rats. The second group of rats was treated with a placebo. The third group of rats was treated with a sophorolipids mixture according to the present invention, such as D-Galactosamine. The results of this testing are shown in Table 4 and Table 5.

TABLE 4

Effect of Sophorolipids on Sprague Dawley Rats

| Group | Survival Data | IL-1 Production | TGF-β1 Production |
|---|---|---|---|
| Cecal ligation alone | ~40% | ~1000 | ~100 |
| Cecal ligation and placebo | ~44% | ~2300 | |
| Cecal ligation and sophorolipids | ~84% | ~1400 | ~110 |

In Table 4, the data has a $P<0.05$, the IL-1 production is in phorsphorlmager units and is the production by splenic lymphocytes, and the TGF-β1 production also is the production by splenic lymphocytes.

TABLE 5

Effect of Sophorolipids on LPS Induced NO Production in Sprague Dawley Rat Macrophage Cell Line

| Treatment | Average uM/L of NO Production |
|---|---|
| Untreated | ~25 |
| LPS | ~130 |
| LPS + SL | ~118 |
| SL | ~10 |

4. Utilizing the Natural Mixture, the Lactonic Fraction, and/or the Non-Lactonic Fraction of Sophorolipids.

The present invention also is a method for producing sophorolipids for the treatment and prophylaxis of sepsis and septic shock and using the natural mixture, the lactonic fraction of the mixture, the non-lactonic fraction of the mixture, and/or combinations of these for the treatment and prophylaxis of sepsis and septic shock. After synthesizing the sophorolipid by fermentation of *Candida bombicola* in a fermentation media to form a natural mixture of lactonic sophorolipids and non-lactonic sophorolipids as disclosed above, one can use the natural mixture for the treatment and prophylaxis of sepsis and septic shock. Alternatively, one can separate the lactonic sophorolipids from the natural mixture to form a lactonic fraction and mixing all remaining fractions to form a non-lactonic fraction and either use the lactonic fraction for the treatment and prophylaxis of sepsis and septic shock and/or use the non-lactonic fraction for the treatment and prophylaxis of sepsis and septic shock.

These methods can use a 17-L-[(2'-O-β-D-glucopyranosyl-β-D-glucopyranosyl)-oxy]-cis-9-octadecenoate based sophorolipid such as 17-L-[(2'-O-β-D-glucopyranosyl-β-D-glucopyranosyl)-oxy]-cis-9-octadecenoate-6',6"-diacetate, Hexyl 17-L[(2'-O-β-D glucopyranosyl-β-D-glucopyranosyl)-oxy]-cis-9-octadecenoate, and Ethyl 17-L[(2'-O-β-D glucopyranosyl-β-D-glucopyranosyl)-oxy]-cis-9-octadecenoate.

5. Delivery Routes and Doses.

The sophorolipid compounds disclosed herein can be delivered in many different forms. Illustrative examples of the delivery forms include intravenous, intraarterially, and intraperitoneal. Those of ordinary skill in the art can chose other delivery systems and formulate the novel sophorolipid into the delivery system chosen without undue experimentation.

Dosages can be determined depending on the particular sepsis or septic shock circumstance, but generally is in the 2-30 mg per kg of body weight range. It is contemplated that persons of ordinary skill in the art could determine an effective amount greater or less than the preferred range depending, as previously mentioned, on the particular sepsis or septic shock circumstance.

6. Combination Systems

The sophorolipids disclosed herein also can be combined in various forms and with other agents for the treatment or prophylaxis of sepsis and septic shock. For example, the sophorolipids disclosed herein can be made and/or used in combination with one or more known agent for the treatment or prophylaxis of sepsis and septic shock to produce alternative agents for the treatment or prophylaxis of sepsis and septic shock. Those of ordinary skill in the art can choose the appropriate or desired known agent for the treatment or prophylaxis of sepsis and septic shock to combine with the sophorolipids to result in an alternate agent for the treatment or prophylaxis of sepsis and septic shock without undue experimentation.

The above detailed description of the preferred embodiments, and the examples, are for illustrative purposes only and are not intended to limit the scope and spirit of the invention, and its equivalents, as defined by the appended claims. One skilled in the art will recognize that many variations can be made to the invention disclosed in this specification without departing from the scope and spirit of the invention.

What is claimed is:

1. A method for treatment of sepsis and septic shock in an human or animal comprising administering a therapeutically appropriate amount of a sophorolipid mixture to a human or animal.

2. The method as claimed in claim 1, wherein the mixture is administered by a method selected from the group consisting of intraperitoneal administration, intraarterial administration, and intravenous administration.

3. The method as claimed in claim 2, wherein the mixture is administered in a dose of between about 2 mg of the mixture per kilogram of the human or animal and about 30 mg of the mixture per kilogram of the human or animal.

4. The method as claimed in claim 1, wherein the mixture comprises a 17-L-[(2'-O-β-D-glucopyranosyl-β-D-glucopyranosyl)-oxy]-cis-9-octadecanoate based sophorolipid.

5. The method as claimed in claim 4, wherein the 17-L-[(2'-O -β-D-glucopyranosyl-β-D-glucopyranosyl)-oxy]-cis-9-octadecenoate is selected from the group consisting of 17-L-[(2'-O-β-D-glucopyranosyl-β-D -glucopyranosyl)-oxy]-cis-9-octadecenoate-6', 6"-diacetate, Hexyl 17- L[(2'-O-β-D glucopyranosyl-β-D-glucopyranosyl)-oxy]-cis-9-octadecenoate, and Ethyl 17-L[(2'-O-β-D glucopyranosyl-β-D-glucopyranosyl)-oxy]-cis-9-octadecenoate.

6. The method as claimed in claim 1, wherein the mixture is administered in a dose of between about 2 mg of the mixture per kilogram of the human or animal and about 30 mg of the mixture per kilogram of the human or animal.

* * * * *